United States Patent [19]

Sumner, Jr. et al.

[11] Patent Number: 5,258,556

[45] Date of Patent: * Nov. 2, 1993

[54] PROCESS FOR THE MANUFACTURE OF 2,2,4,4-TETRAMETHYLCYCLOBUTANEDIOL

[75] Inventors: Charles E. Sumner, Jr.; Bruce L. Gustafson; Jennifer R. Knight, all of Kingsport, Tenn.

[73] Assignee: Eastman Kodak Company, Rochester, N.Y.

[*] Notice: The portion of the term of this patent subsequent to Dec. 8, 2009 has been disclaimed.

[21] Appl. No.: 11,584

[22] Filed: Feb. 1, 1993

[51] Int. Cl.$^5$ .................................... C07C 29/145
[52] U.S. Cl. ............................... 568/839; 568/301; 568/338
[58] Field of Search .................. 568/839, 301, 338

[56] References Cited

U.S. PATENT DOCUMENTS 5,169,994  12/1992  Sumner et al. ................ 568/839

Primary Examiner—Alan Siegel
Attorney, Agent, or Firm—J. Frederick Thomsen; William P. Heath, Jr.

[57] ABSTRACT

Disclosed is a novel process for the manufacture of 2,2,4,4 tetramethylcyclobutane 1,3 diol commencing with the pyrolysis of isobutyric anhydride to produce dimethylketene. Dimethylketene is absorbed into 2,2,4,4 tetramethylcyclobutane 1,3 dione which function as the process solvents for subsequent dimerization of the dimethylketene to 2,2,4,4-tetramethylcyclobutane-1,3-dione followed by the catalytic hydrogenation of the dione to the diol product.

3 Claims, No Drawings

PROCESS FOR THE MANUFACTURE OF 2,2,4,4-TETRAMETHYLCYCLOBUTANEDIOL

This invention pertains to a novel, efficient process for the manufacture of 2,2,4,4 tetramethylcyclobutanediol starting with isobutyric anhydride. More particularly, this invention pertains to a process wherein isobutyric anhydride is converted to dimethylketene which is absorbed into 2,2,4,4 tetramethylcyclobutane-1,3-dione, the dimer of dimethylketene. The dione absorption solvent serves as the process solvent in subsequent dimerization and hydrogenation steps. Another embodiment of the invention pertains to the manufacture of dimethylketene by the pyrolysis of isobutyric anhydride at temperatures significantly lower than those employed in known processes.

2,2,4,4 Tetramethylcyclobutanediol is a valuable monomer which may be used in the preparation of a variety of polymeric materials which possess advantageous properties. For example, polyesters derived from dicarboxylic acids and 2,2,4,4-tetramethylcyclobutanediol possess higher glass transition temperatures and superior weatherability and hydrolytic stability when compared to like polyesters prepared from other commonly used, polyester forming diols.

The preparation of dimethylketene by the pyrolysis of isobutyric anhydride is described in British Patent 965,762. Although the operating conditions such as the pyrolysis temperature, pressure and contact or residence time are broadly described, contact times of less than 1 second and temperatures and pressures of 500 to 600° C. and 100 torr to atmospheric are used in the examples. Mungo et al, Chim. Ind. (Milan), 46 (1), 5–9 (1964) (C. A. 60:9143f) teach the pyrolysis of isobutyric anhydride at an optimum temperature of 625° C. (measured on the wall of the pyrolysis reactor).

British Patent 965,762 also discloses the dimerization of dimethylketene to 2,2,4,4 tetramethylcyclobutanedione but provides essentially no details on the manner in which such dimerization may be carried out or the means by which the dione is recovered. The dimerization of undiluted dimethylketene presents heat transfer problems and thus is potentially hazardous. The Mungo et al reference acknowledges that dimethylketene is very dangerous because of its rapid peroxidation to explosive crystalline material.

U.S. Pat. Nos. 2,936,324 and 3,190,928 described processes for the preparation of 2,2,4,4 tetramethylcyclobutanediol by the hydrogenation of the corresponding dione compound in the presence of nickel and ruthenium catalysts. These patents do not disclose any means by which the hydrogenation processes disclosed therein may be integrated with the dimethylketene manufacturing process.

The process provided by the present invention comprises the manufacture of 2,2,4,4 tetramethylcyclobutanediol from butyric anhydride wherein dimethylketene vapor is absorbed into 2,2,4,4tetramethylcyclobutane ,1,3-dione which then functions as the process solvent for the conversion (dimerization) of dimethylketene to 2,2,4,4 tetramethylcyclobutanedione followed by hydrogenation of the dione to the diol. Thus, our novel process for the manufacture of 2,2,4,4 tetramethylcyclobutanediol comprises the steps of:

(1) feeding isobutyric anhydride to a pyrolysis zone wherein the isobutyric anhydride is heated at a temperature of about 350 to 600° C. to produce a vapor effluent comprising dimethylketene, isobutyric acid and unreacted isobutyric anhydride;

(2) rapidly cooling the vapor effluent to condense isobutyric acid and isobutyric anhydride and separating the condensate from the dimethylketene vapor;

(3) feeding the dimethylketene vapor to an absorption zone wherein the dimethylketene vapor is contacted with and dissolved in a solvent comprising 2,2,4,4 tetramethylcyclobutane 1,3 dione to produce an effluent comprising a solution of dimethylketene in the solvent;

(4) feeding the absorption zone effluent to a dimerization zone wherein dimethylketene is converted to 2,2,4,4 tetramethylcyclobutane 1,3 -dione to produce an effluent consisting essentially of 2,2,4,4-tetramethylcyclobutanedione; and (5) feeding the dimerization zone effluent to a hydrogenation zone wherein the effluent is contacted with a supported hydrogenation catalyst under hydrogenation conditions of pressure and temperature to produce an effluent consisting essentially of 2,2,4,4-tetramethylcyclobutanediol.

The process provides a means for the non-hazardous manufacture of 2,2,4,4-tetramethylcyclobutanediol at good rates and yields, e.g., in yields of 90% or greater based on the butyric anhydride consumed. The use of a melt or liquid form of 2,2,4,4 tetramethylcyclobutane-1,3-dione as the absorbent and dimerization medium is advantageous since it provides a means for obtaining a stream consisting essentially of the dione. When the dione is hydrogenated to 2,2,4,4 tetramethylcyclobutanediol, the removal of an extraneous solvent is not required. Since dimethylketene has a boiling point of 34° C., it is unable to condense in the scrubber and should have the properties of a noncondensible gas. We have discovered that, by maintaining a high temperature in the scrubber, a substantial quantity of the dimethylketene reacts (dimerizes) to form 2,2,4,4 tetramethylcyclobutane-3-dione (the desired product) in the scrubber, thus greatly increasing the efficiency of the scrubber. When the process is practiced in accordance with the present invention, the need for equipment to separate and store an inert organic solvent is eliminated, and the total capital required to operate the process is substantially lowered.

The first step of the process involves feeding isobutyric anhydride, usually in combination with an inert gas such as nitrogen, to the pyrolysis zone wherein the isobutyric anhydride is heated at about 350 to 600° C. under reduced pressure, e.g., 20 to 500 torr. Preferred conditions are temperatures in the range of 400 to 500° C. and pressures of 40 to 250 torr. The contact or residence time of the reactant and product within the pyrolysis zone typically is in the range of about 0.1 to 8 seconds, depending on the temperatures and pressures employed. Step (1) preferably is carried out to achieve an average butyric anhydride conversion of at least 30%, preferably about 50 to 90%.

The second step of the process comprises rapidly cooling the pyrolysis effluent to condense the isobutyric acid by product of the pyrolysis reaction and unreacted butyric anhydride and separating the condensed liquids from the dimethylketene vapor to minimize the reaction of the isobutyric acid and dimethyl ketene. Cooling of the vapor stream may be accomplished using conventional equipment such as one or more heat exchangers or externally cooled cyclones which provide efficient heat removal. The cooling required by the second step normally should reduce the temperature of the pyrolysis effluent to at least 40° C, preferably about 20 to 30° C. The condensed isobutyric acid and isobutyric anhydride may be separated from the gaseous dimethylketene by conventional gas liquid separation means such as one or more cyclones. When the pyrolysis step is carried out under reduced pressure, the temperature reduction and separation of the second step normally are performed at pressures substantially the same as those existing within the pyrolysis zone.

In the third step of our novel process, the highly volatile dimethylketene vapor from the second step is drawn through the vacuum pump(s) and fed to the absorption zone wherein it is contacted with and dissolved in an inert solvent comprising liquid (melted) 2,2,4,4 tetramethylcyclobutane 1,3-dione. The vacuum pump(s) used to reduce the pressure of the pyrolysis or cracking and the cooling separation zones preferably is of a type which does not require a liquid seal. The absorption zone typically is operated at a temperature of about 10 to 150° C., preferably about 115 to 120° C, and a pressure of about 1 to 3 atmospheres absolute to keep the dione extractant in the liquid phase. Essentially all of the dimethylketene absorbed by the dione dimerizes to the dione. Increasing the pressure within the absorption zone generally will result in increased absorption of the dimethylketene.

The absorption zone comprises apparatus which provides for intimate contact between the dimethylketene vapor and the liquid solvent. For example, the apparatus may consist of one or more columns equipped with packing material or trays wherein the dimethylketene vapor is fed at or near the bottom of the column and the solvent is fed at or near the top of the column resulting in the dissolution of the ascending gas by the descending liquid solvent. The flow rate of the dione through the absorber preferably gives a 4% solution of dimethylketene.

The dimerization zone of the fourth step may comprise any apparatus which permits the step (3) effluent to be maintained at a temperature of about 120 to 140° C. for a period of time, e.g., a residence time of about 50 to 80 minutes, sufficient to convert substantially all of the dimethylketene in the effluent to 2,2,4,4-tetramethylcyclobutanedione. Thus, the dimerization zone may consist of an agitated vessel equipped with means to heat the step (3) effluent. The product effluent of the dimerization zone consists essentially of 2,2,4,4 tetramethylcyclobutanedione. A portion of the product dione equivalent to the amount of dimethylketene fed to the absorption zone is fed to the hydrogenation zone. The remaining dione is recirculated to the absorption zone.

The final step of our process comprises the hydrogenation of the 2,2,4,4 tetramethylcyclobutanedione present in the step (4) effluent wherein the effluent is contacted with hydrogen at hydrogenation conditions of pressure and temperature in the presence of a hydrogenation catalyst, i.e., a catalyst which is effective to promote the hydrogenation of carbonyl compounds to their corresponding alcohols such as Raney nickel, Raney cobalt molybdenum promoted nickel, copper chromite and supported Group VIII metals. The hydrogenation preferably is carried out in the presence of a supported catalyst such as nickel on alumina, nickel on silica, ruthenium on carbon or alumina, platinum on alumina and platinum on carbon. The supported nickel catalyst is especially preferred. The hydrogenation conditions may be selected from temperatures and pressures in the range of about 100 to 2000 psig and 130 to 200° C. The conditions preferably are in the range of about 300 to 400 psig and 130 to 180° C.

The 2,2,4,4 tetramethylcyclobutanediol obtained from the hydrogenation step in accordance with the process described hereinabove may be isolated by means of conventional distillation and or crystallization procedures. If necessary, the product diol may be distilled, optionally under reduced pressure, to obtain substantially pure 2,2,4,4-tetramethylcyclobutanediol.

The present invention also provides a process for the manufacture of dimethylketene by contacting, for greater than 1 second, isobutyric anhydride at a temperature of about 350 to 450° C. and a pressure of less than 500 torr. In addition to lowering operating costs, the use of a lower temperature results in the formation of less decomposition products, thereby increasing the yield of dimethylketene based on the isobutyric anhydride converted. This embodiment of our invention preferably employs a contact time of about 0.01 to 10 seconds at 350 to 450° C. and a pressure of about 50 to 250 torr.

The processes provided by the present invention are further illustrated by the following examples. The apparatus used in the examples included a pyrolysis preheater consisting of a 3 foot section of 0.25 inch outside diameter, stainless steel tubing coiled inside a heating block. The preheater tubing was connected to the pyrolysis zone which consisted of a seven foot section of 0.25 inch outside diameter, stainless steel tubing, also coiled inside a heating block. The volume of the preheater was 13 mL and the volume of the pyrolysis zone was 29 mL. The pyrolysis tube was connected to a tube in shell heat exchanger which served to quench the hot gasses exiting the pyrolysis zone. The heat exchanger was a 3 inch by 0.25 inch stainless steel tube inside a steel jacket containing a flow of water at 25° C. The gasses and liquid exited the tube into a void space having a glass tube for a drain for liquid and a side arm for the gasses to escape. All metal to glass connections were made using 0.375 inch swedgelock and graphite ferrules. The side arm was connected directly to a glass cyclone separator. The separator was jacketed with a flow of water at 25° C. The volume of the separator was 122 mL with a 5 mm diameter exit and 1 mm diameter entrance. The length was 14 cm with a diameter of 5 cm at the widest part (top). The exit tube of the cyclone separator was connected to the first vacuum pump by a 12 inch section of flexible steel tubing. The vacuum was achieved by means of 2 Air Dimensions Inc. model 19710T Dia-ac pumps hooked together in series. The maximum vacuum attainable was determined to be 67 Torr. The exit port of the pump was connected to the absorber by means of a 12 inch flexible steel tube swedged to a sidearm adaptor situated between the scrubber and reactor. The noncondensible gasses from the cracker (including dimethylketene) were pumped from the pyrolysis zone to the absorption zone through the exit port of the second pump. The pressure inside the cracker was measured by an electronic pressure gauge situated at the top of the preheater. Any off-gas that passed through the scrubber went through a bubbler full of ethanol and was measured by means of an electronic flow sensor.

The absorption and dimerization zones comprised a jacketed scrubber, jacketed reactor, and electrically traced feed lines and take off lines. The scrubber comprised a 14 × 1 inch jacketed Pyrex glass tube containing glass helixes. The free volume of the scrubber was 200 mL. The scrubber was vented to a 300 mL flask through a 0.25 inch, electrically heat-traced, stainless steel tube. The flask was vented to a Firestone valve, a glass bubbler filled with ethanol, and a digital flow monitor connected with Tygon tubing. The flask served to collect dimethylketene that was not absorbed in the scrubber and also to collect 2,2,4,4 tetramethylcyclobutanedione that sublimed from the top of the scrubber. The temperature inside the scrubber was maintained by a circulating oil bath. The scrubber was positioned over the reactor which was a series of 7 glass bulbs connected by a 4 mm inside diameter tube. The reactor was positioned inside a glass jacket and the temperature was maintained by a circulating oil bath. The volume of the reactor was 1.04 L. Material was removed from the bottom of the reactor through a 0.125 inch, heat traced, stainless steel tube running through a metering pump to a "T". One line of the "T" led to a product collection vessel and the other led to the top of the scrubber. This configuration allowed material to be circulated through the system at a range of temperatures.

The 2,2,4,4 tetramethylcyclobutane 1,3 dione was transferred to the hydrogenation zone which consisted of a 1 L stainless steel autoclave equipped with a stirrer and a catalyst basket. The material charged to the hydrogenation zone was a mixture of 2,2,4,4-tetramethylcyclobutane 1,3-dione and 300 g of 2,2,4,4-tetramethylcyclobutane 1,3-diol.

In operation, the preheater and pyrolysis tube were evacuated and heated to the desired temperatures. Usually, only the temperature of the pyrolysis tube was varied; the temperature of the preheater was constant at 350° C. Isobutyric anhydride was pumped to the preheater at a known rate. Dimethylketene exited the pump and was captured in the absorber operation and converted to dione in the reactor. The product was taken from the stream exiting the reactor that was sent to the scrubber. The product was taken off at a rate so as to maintain a constant level in the reactor. The conversion to dimethylketene was determined by measuring the ratio of isobutyric acid to isobutyric anhydride condensed from the cracker effluent.

EXAMPLE 1

Isobutyric anhydride was fed to the preheater at a rate of 0.0127 mole (2.0 g) per minute for 150 minutes. The pyrolysis temperature and pressure were 455° C. and 87 Torr. The temperature within the absorption was maintained at 117° C. and the dimerization reactor temperature was 137° C. The circulation rate of 2,2,4,4-tetramethylcyclobutane-1,3 -dione to the absorber was 14 mL/minute. No off-gas was observed to be produced in the pyrolysis zone by visual observation of the exit bubbler or recorded by the digital flow monitor. No dimethylketene was observed to exit the absorber column. At the end of the run, the conversion to dimethylketene was found to be 43.6%. The amount of dimethylketene produced per volume of absorber fluid circulated to the top of the absorber was calculated to be 0.03 g/mL. Approximately 63 g of 2,2,4,4-tetramethylcyclobutane-1,3-dione was produced.

The autoclave comprising the hydrogenation zone was charged with 30 mL of a catalyst comprising nickel on a silica/alumina support, 80 g of 2,2,4,4-tetramethylcyclobutane 1,3-dione and 300 g of 2,2,4,4 tetramethyl cyclobutane I,3 diol. The autoclave was sealed, flushed with nitrogen, heated to 145° C. and pressurized with hydrogen to 700 psi. The temperature and pressure were maintained for 8 hours and thereafter the autoclave was cooled to room temperature and vented. The yield of solid product having a purity of 97% was 293 g.

EXAMPLE 2

Isobutyric anhydride was fed to the preheater at a rate of 0.025 mole (4.0 g) per minute for 180 minutes. The pyrolysis temperature and pressure were 455° C. and 105 Torr. The temperature of the absorber was maintained at 117° C. and the reactor temperature was 140° C. The circulation rate 2,2,4,4-tetramethylcyclobutane-1,3-dione to the absorber was 22 mL/minute. No off-gas was observed to be produced in the cracker by visual observation of the exit bubbler or recorded by the digital flow monitor. No dimethylketene was observed to exit the scrubber column. At the end of the run, the conversion to dimethylketene was found to be 42.3%. The amount of dimethylketene produced per volume of absorber fluid circulated to the top of the absorber was calculated to be 0.034 g/mL. Approximately 135 g of 2,2,4,4-tetramethylcyclobutane-1,3-dione was produced.

EXAMPLE 3

Isobutyric anhydride was fed to the preheater at a rate of 0.025 mole (4.0 g) per minute for 120 minutes. The pyrolysis temperature and pressure were 495° C., and 123 Torr. The temperature of the absorber was maintained at 115° C. and the reactor temperature was 141I° C. The circulation rate 2,2,4,4-tetramethylcyclobutane-1,3-dione to the absorber was 22 mL/minute. Periodic formation of off gas in the pyrolysis zone was observed and recorded by the digital flow monitor. Dimethylketene was observed to exit the scrubber column and accumulate in the collection flask coincidental with the formation of off gas. At the end of the run, the conversion to dimethylketene was found to be 54.0%. The amount of dimethylketene produced per volume of scrubber fluid circulated to the top of the scrubber was calculated to be 0.044 g/mL.

The invention has been described in detail with particular reference to preferred embodiments thereof, but it will be understood that variations and modifications can be effected within the spirit and scope of the invention.

We claim:

1. Process for the manufacture of 2,2,4,4-tetramethylcyclobutane- 1,3-diol which comprises the steps of:
   (1) feeding isobutyric anhydride to a pyrolysis zone wherein the isobutyric anhydride is heated at a temperature of about 350 to 600° C. to produce a vapor effluent comprising dimethylketene, isobutyric acid and unreacted isobutyric anhydride;
   (2) rapidly cooling the vapor effluent to condense isobutyric acid and isobutyric anhydride and separating the condensate from the dimethylketene vapor;
   (3) feeding the dimethylketene vapor to an absorption zone wherein the dimethylketene vapor is contacted with and dissolved in a solvent comprising 2,2,4,4-tetramethylcyclobutane-1,3-dione to produce an effluent comprising a solution of dimethylketene in the solvent;
   (4) feeding the absorption zone effluent to a dimerization zone wherein the dimethylketene is converted to 2,2,4,4 tetramethylcyclobutane-1,3-dione to produce an effluent consisting essentially of 2,2,4,4 tetramethylcyclobutane 1,3 dione; and (5) feeding the dimerization zone effluent to a hydrogenation zone wherein the effluent is contacted with a supported hydrogenation catalyst under hydrogenation conditions of pressure and temperature to produce an effluent comprising a solution of 2,2,4,4-tetramethylcyclobutane 1,3-diol in the solvent.

2. Process of claim 1 wherein isobutyric anhydride is heated at a temperature of about 44 to 500° C. and a pressure of about 40 to 250 torr in the pyrolysis zone and the absorption and dimerization zones are maintained at about 110 to 140° C.

3. Process according to claim 1 wherein the the absorption zone is maintained at a temperature of about 115 to 120° C., and a pressure of about 1 to 3 atmospheres absolute.

* * * * *